United States Patent
Zak

(10) Patent No.: US 7,414,164 B2
(45) Date of Patent: Aug. 19, 2008

(54) DIISOBUTYLENE PROCESS

(75) Inventor: Thomas S. Zak, West Chester, PA (US)

(73) Assignee: Lyondell Chemical Technology, L.P., Houston, TX (US)

(*) Notice: Subject to any disclaimer, the term of this patent is extended or adjusted under 35 U.S.C. 154(b) by 564 days.

(21) Appl. No.: 11/112,502

(22) Filed: Apr. 22, 2005

(65) Prior Publication Data
US 2006/0241326 A1  Oct. 26, 2006

(51) Int. Cl.
*C07C 2/04* (2006.01)
*C07C 2/28* (2006.01)

(52) U.S. Cl. .......... 585/515; 585/329; 585/510; 585/526

(58) Field of Classification Search .......... 585/515, 585/329, 510, 526
See application file for complete search history.

(56) References Cited

U.S. PATENT DOCUMENTS

| | | | |
|---|---|---|---|
| 3,351,635 A | 11/1967 | Kollar | 260/348.5 |
| 3,510,538 A | 5/1970 | Rosenthal | 260/682 |
| 4,100,220 A | 7/1978 | Bowman et al. | 260/683 |
| 4,155,945 A | 5/1979 | Levine | 585/639 |
| 4,165,343 A | 8/1979 | Levine et al. | 585/638 |
| 4,447,668 A | 5/1984 | Smith, Jr. et al. | 585/639 |
| 5,276,239 A * | 1/1994 | Sanderson et al. | 582/511 |
| 5,625,109 A | 4/1997 | Gupta | 585/639 |
| 5,877,372 A | 3/1999 | Evans et al. | 585/510 |
| 6,376,731 B1 | 4/2002 | Evans et al. | 585/510 |

OTHER PUBLICATIONS

Simga-Aldrich Catalog, Amberlyst 15 hydrogen form, 2007. (website www.sigmaaldrich.com).*

* cited by examiner

*Primary Examiner*—Glenn Caldarola
*Assistant Examiner*—In Suk Bullock
(74) *Attorney, Agent, or Firm*—Kevin M. Carroll

(57) ABSTRACT

This invention is a process for producing diisobutylene from isobutylene. The process comprises first forming dry sulfonic acid resin by contacting water wet sulfonic acid resin catalyst with a first reaction feed comprising isobutylene under conditions effective to produce tertiary butyl alcohol from the reaction of isobutylene and water, and then contacting the dry sulfonic acid resin with a second reaction feed comprising isobutylene under conditions effective to oligomerize isobutylene to produce diisobutylene.

15 Claims, No Drawings

DIISOBUTYLENE PROCESS

FIELD OF THE INVENTION

This invention relates to a process for producing diisobutylene from isobutylene. The process comprises first forming dry sulfonic acid resin by contacting water wet sulfonic acid resin catalyst with a first reaction feed comprising isobutylene under conditions effective to produce tertiary butyl alcohol from the reaction of isobutylene and water, and then contacting the dry sulfonic acid resin with a second reaction feed comprising isobutylene under conditions effective to oligomerize isobutylene to produce diisobutylene.

BACKGROUND OF THE INVENTION

The oligomerization of olefins such as isobutylene using a sulfonic acid-type ion exchange resin catalyst is well-known in the art. For instance, U.S. Pat. No. 4,100,220 describes isobutylene oligomerization using a sulfonic acid resin catalyst and tertiary butyl alcohol selectivity enhancing modifier. In addition, U.S. Pat. No. 4,447,668 discloses isobutylene oligomerization using sulfonic acid resin catalyst A-15 with methyl t-butyl ether as solvent. Further, U.S. Pat. No. 5,877,372 describes the selective oligomerization of isobutylene using a sulfonic acid resin catalyst, tertiary butyl alcohol selectivity enhancing modifier and isooctane diluent. Lastly, U.S. Pat. No. 6,376,731 discloses the oligomerization of isobutylene in the presence of a $C_3$-$C_4$ alkane diluent to enhance oligomerization selectivity and tertiary butyl alcohol to promote selectivity to diisobutylene.

The diisobutylene product may be used as such or may be hydrogenated to isooctane as described in U.S. Pat. Nos. 5,877,372 and 6,376,731. Diisobutylene and isooctane are potential fuel blending compositions.

Sulfonic acid ion exchange resins for isobutylene oligomerization are typically supplied as water wet resins containing greater than 50 wt. % water. Unfortunately, the presence of water hinders the oligomerization reaction. In order for the sulfonic acid resin to be active in isobutylene oligomerization, the sulfonic acid resin must be dried. Typically, the resin is dried by vacuum or by heat to remove the water from the resin or the resin may be contacted with a solvent to remove the water from the resin. The solvent contact is performed using an organic liquid or reactant feed and is performed under ambient conditions. The vacuum or heat drying method adds unwanted cost to the process and the solvent contact method requires an inordinate amount of time to dry the resin.

In sum, new methods to produce diisobutylene by oligomerization of isobutylene over a sulfonic acid-type ion exchange resin catalyst are needed. Particularly needed are processes for drying the sulfonic acid resin catalyst prior to the oligomerization step.

SUMMARY OF THE INVENTION

This invention is a process for producing diisobutylene. The process comprises first forming dry sulfonic acid resin by contacting water wet sulfonic acid resin catalyst with a first reaction feed comprising isobutylene under conditions effective to produce tertiary butyl alcohol by the reaction of isobutylene and water, and then contacting the dry sulfonic acid resin with a second reaction feed comprising isobutylene under conditions effective to produce diisobutylene. I have found that the method to dry the water wet sulfonic acid resin and oligomerize isobutylene is an efficient process to produce diisobutylene.

DETAILED DESCRIPTION OF THE INVENTION

The process of the invention comprises oligomerizing isobutylene over a sulfonic acid-type ion exchange resin catalyst to produce diisobutylene. Sulfonic acid resin catalysts are well known. Commercial examples of sulfonic acid resin catalysts include Amberlyst A-15, Amberlyst A-35, Dowex 50, Duolite C20, Lewatit K2431, Purolite CT175, Purolite CT275, and the like. The oligomerization of isobutylene using sulfonic acid resin catalysts is well known in the art and has been described in U.S. Pat. Nos. 4,100,220, 4,447,668, 5,877,372, and 6,376,731, the teachings of which are hereby incorporated by reference.

The process of the invention comprises first forming dry sulfonic acid resin by contacting wet sulfonic acid resin catalyst with a first reaction feed comprising isobutylene under conditions effective to produce tertiary butyl alcohol by the reaction of isobutylene and water. Sulfonic acid resin catalysts such as Amberlyst A-15 and A-35 are supplied in their water wet form. Unfortunately, the presence of water hinders the oligomerization of isobutylene and the resin must be dried prior to use. The process of the invention comprises a method to dry wet resin for use in isobutylene oligomerization. The wet resin is contacted with a first reaction feed comprising isobutylene under conditions effective to produce tertiary butyl alcohol by reaction of isobutylene and water. Suitable conditions include temperatures broadly in the range 35° C. to 100° C., preferably 40° C. to 80° C. Suitable pressures include pressures sufficient to maintain the liquid phase, preferably above 50 psig, most preferably from 50 to 500 psig. The reaction of water and isobutylene effectively dries the wet sulfonic acid resin by producing tertiary butyl alcohol which is removed from the reactor with the product stream.

The first reaction feed may include any source of isobutylene, including Cat B-B (sometimes known as Refinery B-B), raffinate streams, and isobutylene produced by the dehydration of tertiary butyl alcohol as described in U.S. Pat. Nos. 5,625,109, 3,510,538, 4,165,343, and 4,155,945. The production of tertiary butyl alcohol by means of the Oxirane process is well known and widely practiced on an industrial scale. See, for example, U.S. Pat. No. 3,351,635.

The first reaction feed preferably contains certain diluents in addition to isobutylene, especially when the first reaction feed is also used as the second reaction feed to the oligomerization step. The presence of diluents is preferred. Tertiary butyl alcohol is preferably contained in the first reaction feed as a selectivity enhancing modifier for isobutylene oligomerization. The use of tertiary butyl alcohol in isobutylene oligomerization is taught in U.S. Pat. Nos. 4,100,220, 5,877,372, and 6,376,731. Preferably, the first reaction feed contains at least 0.2 weight percent tertiary butyl alcohol, most preferably from 1 to 10 weight percent tertiary butyl alcohol. In addition, the first reaction feed may also contain a $C_3$-$C_{10}$ alkane diluent in order to further enhance oligomerization selectivity by reducing isobutylene feed concentration, and to aid in removal of the reaction exotherm. Preferably, the alkane diluent is isooctane. The use of alkane diluents in isobutylene oligomerization is taught in U.S. Pat. Nos. 5,877,372 and 6,376,731. If an alkane diluent is used, the first reaction feed will preferably contain 30 to 80 weight percent alkane.

After drying the wet sulfonic acid resin catalyst, diisobutylene is then produced by contacting the dry resin with a second reaction feed containing isobutylene under conditions effective to oligomerize isobutylene. Generally small amounts of trimer are also formed in the oligomerization reaction. Usually, less than 10% of the converted isobutylene is converted into triisobutylene coproduct. In general, known oligomerization conditions can be employed in the oligomerization step. Suitable conditions include temperatures broadly in the range 50° C. to 200° C., preferably 60° C. to 150° C. Suitable pressures include those pressures sufficient to maintain the liquid phase, preferably above 50 psig, most preferably from 50 to 500 psig.

The second reaction feed may include any source of isobutylene, including Cat B-B (sometimes known as Refinery B-B), raffinate streams, and isobutylene produced by the dehydration of tertiary butyl alcohol. The second also preferably contains certain diluents in addition to isobutylene. Tertiary butyl alcohol is preferably contained in the second reaction feed. Preferably, the second reaction feed contains at least 0.2 weight percent tertiary butyl alcohol, most preferably from 1 to 10 weight percent tertiary butyl alcohol. In addition, the second reaction feed may also contain a $C_3$-$C_{10}$ alkane diluent. Preferably, the alkane diluent is isooctane. If an alkane diluent is used, the second reaction feed will preferably contain 30 to 80 weight percent alkane.

The drying step may be performed in a first vessel and then the dry sulfonic acid resin transported to a second vessel for the oligomerization step. Preferably, the drying and oligomerization steps are performed in the same reactor vessel. Most preferably, the drying and oligomerization steps are performed in a continuous step-wise manner in the same reactor vessel, wherein the first and second reaction feeds are the same.

The oligomerization product contains diisobutylene as well as some unreacted isobutylene and triisobutylene coproduct. It may be necessary to separate the diisobutylene from isobutylene using conventional procedures. If isobutylene is separated from the diisobutylene product, the isobutylene may be recycled back to the oligomerization reactor.

Following the production of diisobutylene, the diisobutylene is optionally hydrogenated to isooctane. The hydrogenation step can be carried out using conventional methods. For example, the diisobutylene may be brought into contact with hydrogen in the liquid phase at moderate temperatures and pressures. Suitable reaction temperatures vary from 0° C. to 500° C., but preferably from 25° C. to 200° C. The reaction is preferably conducted at or above atmospheric pressure. The precise pressure is not critical. Typical pressures vary from 1 atmosphere to 100 atmospheres. Any suitable hydrogenation catalyst may be used, including but not limited to Raney nickel and supported nickel, palladium, and platinum catalysts. Suitable supports for nickel, palladium, and platinum include carbon, silica, alumina, diatomaceous earth, and the like. Preferably, the hydrogenation catalyst is a supported nickel catalyst. The hydrogenation may be performed in the presence or absence of a solvent. Following hydrogenation, the isooctane product can be recovered by removing the hydrogenation catalyst and the solvent (if present) in a conventional manner, to separate isooctane.

The hydrogenation reaction may be performed using any of the conventional reactor configurations known in the art for such hydrogenation processes. Continuous as well as batch procedures may be used. For example, the catalyst may be deployed in the form of a fixed bed or slurry.

The following examples merely illustrate the invention. Those skilled in the art will recognize many variations that are within the spirit of the invention and scope of the claims.

EXAMPLE 1

In Situ Drying of Wet Resin and Dimerization of Isobutylene

An isobutylene reaction feed comprising isobutylene (36 wt. %), tertiary butyl alcohol (3.3 wt. %), and isooctane (balance) is fed to a plug flow reactor containing water wet sulfonic acid resin catalyst (30 cc, LHSV=5 $h^{-1}$, recycle/fresh=1,400 psig, 65° C.). This isobutylene reaction feed is used as both the first reaction feed for drying the wet sulfonic acid resin and the second reaction feed in the oligomerization step. The reactor is maintained at 65° C. and the product stream is analyzed by GC at 2, 3, 4, 5, 6, 7, 8.5 and 10 hours following reaction start-up. Product analysis shows that a significant amount of tertiary butyl alcohol is formed during the first 7 hours after reaction start-up indicating that the bed is drying very quickly. At 8.5 hours, the tertiary butyl alcohol in the product stream is 3.6 wt. % and at 10 hours is at 3.41 wt. %, barely above the amount fed to the reactor. By 6 hours after reaction start-up, diisobutylene is produced in significant quantities (5.8 wt. %) and is found at 17.4 wt. % of the product stream by 10 hours.

The results indicate that wet sulfonic acid resin can be quickly dried by removing water through its reaction with isobutylene to form tertiary butyl alcohol. The dried resin is then an effective oligomerization catalyst.

I claim:

1. A process comprising:
    (a) contacting a wet sulfonic acid resin catalyst with a first reaction feed comprising isobutylene under conditions effective to produce tertiary butyl alcohol, wherein a dry sulfonic acid resin catalyst is produced; and
    (b) contacting the dry sulfonic acid resin catalyst with a second reaction feed comprising isobutylene under conditions effective to oligomerize isobutylene to produce diisobutylene.

2. The process of claim 1 wherein the wet sulfonic acid resin catalyst is contacted with the first reaction feed at a temperature of 35° C. to 100° C.

3. The process of claim 1 wherein the dry sulfonic acid resin catalyst is contacted with the second reaction feed at a temperature of 50° C. to 200° C.

4. The process of claim 1 wherein the isobutylene of the first reaction feed is produced by the dehydration of tertiary butyl alcohol.

5. The process of claim 1 wherein the isobutylene of the second reaction feed is produced by the dehydration of tertiary butyl alcohol.

6. The process of claim 1 wherein the first reaction feed additionally comprises at least 0.2 weight percent tertiary butyl alcohol.

7. The process of claim 6 wherein the first reaction feed contains 1 to 10 weight percent tertiary butyl alcohol.

8. The process of claim 1 wherein the first reaction feed additionally comprises a $C_3$-$C_{10}$ alkane.

9. The process of claim 8 wherein the $C_3$-$C_{10}$ alkane is isooctane.

10. The process of claim 1 wherein the second reaction feed additionally comprises at least 0.2 weight percent tertiary butyl alcohol.

11. The process of claim 10 wherein the second reaction feed contains 1 to 10 weight percent tertiary butyl alcohol.

12. The process of claim 1 wherein the second reaction feed additionally comprises a $C_3$-$C_{10}$ alkane.

13. The process of claim 12 wherein the $C_3$-$C_{10}$ alkane is isooctane.

14. The process of claim 1, further comprising hydrogenating the diisobutylene in the presence of a hydrogenation catalyst to form isooctane.

15. The process of claim 14 wherein the hydrogenation catalyst is a supported nickel catalyst.

* * * * *